United States Patent [19]

Kanamori

[11] Patent Number: 4,817,446
[45] Date of Patent: Apr. 4, 1989

[54] PARTICLE SIZE DISTRIBUTION ANALYSIS

[75] Inventor: Shigeo Kanamori, Kobe, Japan

[73] Assignee: Toa Medical Electronics Co. Ltd., Japan

[21] Appl. No.: 14,770

[22] Filed: Feb. 13, 1987

[30] Foreign Application Priority Data

Jul. 25, 1986 [JP] Japan ................................ 61-176423
Jul. 25, 1986 [JP] Japan ................................ 61-176424
Jul. 25, 1986 [JP] Japan ................................ 61-176425

[51] Int. Cl.$^4$ .......................................... G01N 15/02
[52] U.S. Cl. .................................... 73/865.5; 364/555
[58] Field of Search ......................... 73/865.5; 364/555

[56] References Cited

U.S. PATENT DOCUMENTS

| | | | |
|---|---|---|---|
| 3,449,567 | 6/1969 | Olivier et al. | 73/865.5 X |
| 3,779,070 | 12/1973 | Cushman et al. | 73/865.5 |
| 3,812,335 | 5/1974 | Coulter et al. | 364/535 |
| 3,877,311 | 4/1975 | Sugawara et al. | 73/865.5 |
| 3,944,797 | 3/1976 | Coulter et al. | 364/555 |
| 4,128,884 | 12/1978 | England | 364/555 X |
| 4,288,162 | 9/1981 | Sakamoto et al. | 356/335 |
| 4,329,053 | 5/1982 | Fymant | 356/338 X |
| 4,453,226 | 6/1984 | Hobbs et al. | 364/555 |
| 4,526,029 | 7/1985 | Starnes | 73/865.5 X |
| 4,676,641 | 6/1987 | Bott | 356/340 X |
| 4,706,207 | 11/1987 | Hennessy et al. | 364/555 |

FOREIGN PATENT DOCUMENTS 47-13299 4/1972 Japan .

OTHER PUBLICATIONS

"A Forward Angle Light Scattering Camera for Determining Size Distribution in Aerosols"; *The Review of Scientific Instruments*, vol. 25, No. 10, pp. 1004–1010; Oct. 1954; Pui–Kum Lee et al.

"Particle Size Analysis and Analyzers"; *Chemical Engineering*, pp. 149–156, 5/20/1968; C. E. Lapple.

"Time of Flight Aerosol Beam Spectrometry: A New Technique for Measuring Airborne Particulates"; Proceedings of the 12th Int. Colloquium on Atmospheric Pollution; May 1976, pp. 271–277; Barton Dahneke.

"A Dynamic Compensation for Static Particle Size Distribution Estimators"; I.S.A. Transactions, vol. 25, No. 1, pp. 47–51; pub. by Mar. 1986; G. Gonzalez et al.

Primary Examiner—Tom Noland
Attorney, Agent, or Firm—Barnes & Thornburg

[57] ABSTRACT

A method for measuring and analyzing particle size distribution of extremely fine particles, such as blood corpuscles and cells, comprises collecting analyzing particle size distribution from the instrument, setting an estimated distribution theoretically, comparing between the two distributions, determining the difference therebetween, and making the difference a characteristic parameter for the analyzing particle size distribution.

16 Claims, 10 Drawing Sheets

RBC=445×10⁴/mm³

RBC=512×10⁴/mm³

PARTICLE SIZE DISTRIBUTION ANALYSIS

BACKGROUND AND SUMMARY OF THE INVENTION

The present invention relates to a method for measuring and analyzing particle size distributions, wherein the particles include blood corpuscles, various cells, latex particles or any other fine particles.

The measurement and analysis of blood corpuscles are known in the art, but it is uncommon that they are applied to a clinical diagnosis. This is because of the difficulty and inaccuracy involved in conducting them. However the recent development of a fluid control system, such as sheath flow control system, has enhanced the accuracy of an automatic measuring method of particle size distributions, and has facilitated the application of the method for clinical purposes. At the same time this has aroused people's attention to the importance of analysis of particle size distribution.

One example of the conventional analyses is disclosed in Japanese Patent Unexamined Publication No. 47(1972)-13299. This prior art method is to analyze the particle size distribution of red blood cells, and is characterized by the representation of the distribution area in terms of quartile variable coefficients.

With respect to the particle size distribution of blood platelets it is presumed that the blood platelets are in a log-normal distribution, and then those which are not in agreement with the presumption are considered as abnormal, which is commonly called a 'Curve Fit' method. The feature of the first-mentioned prior art method for red blood cells resides in the indication of the width of the distribution on presumption that the particle size distribution of red blood cells is constantly uniform. In addition, the blood corpuscles are readily affected by dirt and dead cells. For these reasons an inaccurate measurement may result. Furthermore, the blood corpuscles unavoidably contain noise components, so that the thresholds are used to count the number of corpuscles. Nevertheless, when a noise component and a corpuscle overlap or two or more corpuscles overlap each other, the resulting measurement may be inaccurate.

The 'Curve Fit' method determines the abnormality of blood platelets on presumption that they are in the log-normal distribution but does not represent the degree of abnormality numerically, that is, in an objective manner.

In order to solve the problems pointed out above, The International Committee for Standardization in Haematology (ICSH) issued an official recommendation in 1982, in which the theoretical distribution should be applied to particle size distributions. The Committee also gave a general statement in support of its recommendation.

In spite of these efforts no practical system of measuring and analyzing particle size distributions has yet been accomplished for the clinical uses.

An object of the present invention is overcoming the difficulties pointed out above, and is to provide a system for measuring and analyzing particle size distribution accurately and readily so as to serve practical purposes, such as clinical diagnosis.

Another object of the present invention is to provide a system for measuring and analyzing particle size distribution, the system being carried out in a limited space without employing a large-size instrumental aid.

These objects are achieved by providing a method for measuring and analyzing particle size distribution. The method includes collecting an analyzing particle size distribution of a given sample content from a particle size measuring instrument. An estimated particle size distribution is set up as a theoretical distribution. The next step includes comparing between the analyzing particle size distribution and the estimated particle size distribution so as to determine the difference between the two. Finally, the difference is made a characteristic parameter for classifying the analyzing particle size distribution according to the sample content.

According to other advantageous features of certain preferred embodiments of the invention, after the estimated particle size distribution is set up as a theoretical distribution, the analyzing distribution and the estimated distribution are compared to set up a classifying characteristic parameter representing the difference therebetween. The analyzing particle distribution content is classified according to the sample content depending upon at least one of the characteristic parameter and the type of estimated distribution.

According to other advantageous features of certain preferred embodiments of the invention, a plurality of estimated particle size distributions are used in the comparing step. In certain preferred embodiments, the number of estimated particle size distributions is determined as a function of the analyzing particle size distribution.

According to other advantageous features of certain preferred embodiments of the invention, a method is provided which includes collecting an analyzing particle size distribution from a particle size measuring instrument, and setting up an estimated particle size distribution as a theoretical distribution as a function of the collected analyzing particle size distribution.

According to the other advantageous features of certain preferred embodiments of the invention, the setting up of the estimated particle size distribution includes setting up a logarithm of the frequency of the analyzing particle size distribution, differeniating the logarithm of the frequency of the analyzing particle size distribution, finding a linear portion of the logarithm of the frequency of the analyzing particle size distribution, calculating a mean value and standard deviation from the linear portion and determining the estimated particle size distribution using the calculated mean value and the standard deviation.

Further objects, features and advantages of the present invention will become more apparent from the following description when taken with the accompanying drawings which show, for the purposes of illustration only, embodiments constructed in accordance with the present invention.

DETAILED DESCRIPTION OF THE DRAWINGS

To carry out the method of the present invention an instrument is used to measure particle size distributions. The instrument referred to herein is a device which allows a suspension containing fine particles to pass through the minute pore produced therein, detects the particles by electric or optical differences between the liquid and the particles, generates pulses in proportion to the amplitude (volume) of the particles, and converts the signals into a particle size distribution.

EXAMPLE 1

This is an example in which the method of the present invention was applied to the analysis of a particle size distribution of blood corpuscles, employing a log-normal distribution, which is expressed by:

$$f(x) = \frac{1}{x\sigma\sqrt{2\pi}} \exp\left(-\frac{(\ln x - \mu)^2}{2\sigma^2}\right)$$

wherein $\mu$ is a mean value, and $\sigma$ is a standard deviation. The natural logarithm of the f(x) is then expressed by:

$$\ln f(x) = \ln\frac{1}{x\sigma\sqrt{2\pi}} - \frac{(\ln x - \mu)^2}{2\sigma^2}$$

$$= -\ln x + \ln\frac{1}{\sigma\sqrt{2\pi}} - \frac{(\ln x)^2}{2\sigma^2} +$$

$$\frac{(\ln x)\mu}{\sigma^2} - \frac{\mu^2}{2\sigma^2}$$

In the following discussion, X and g(x) are substituted for $\ln x$ and $\ln f(x)$, respectively.

$$g(x) = -\frac{1}{2\sigma^2}X^2 + \frac{\mu - \sigma^2}{\sigma^2}X + \ln\frac{1}{\sigma\sqrt{2\pi}} - \frac{\mu^2}{2\sigma^2}$$

In this way g(x) is expressed by a quadratic expression with respect to X. Herein, g(x) is differentiated as follows:

$$g'(x) = -\frac{1}{\sigma^2}X + \frac{\mu - \sigma^2}{\sigma^2}$$

$$= -\frac{1}{\sigma^2}(X - \mu + \sigma^2)$$

Thus g'(x) is expressed by a linear expression which intersects the X axis at $\mu - \sigma^2$ and which is inclined thereto at $-(1/\sigma^2)$. From this the value of g'(x), the mean value $\mu$ and the standard deviation $\sigma$ are calculated. In this way the log-normal distribution curve is estimated.

As an example of a parameter representing the difference between the estimated log-normal distribution and the particle size distribution of the original blood corpuscles the matching distance (D) is introduced, which is defined as follows:

$$D = \int (|f(x) - H(x)|) dx$$

wherein f(x) is the given distribution and h(x) is the estimated one.

Figure 1:
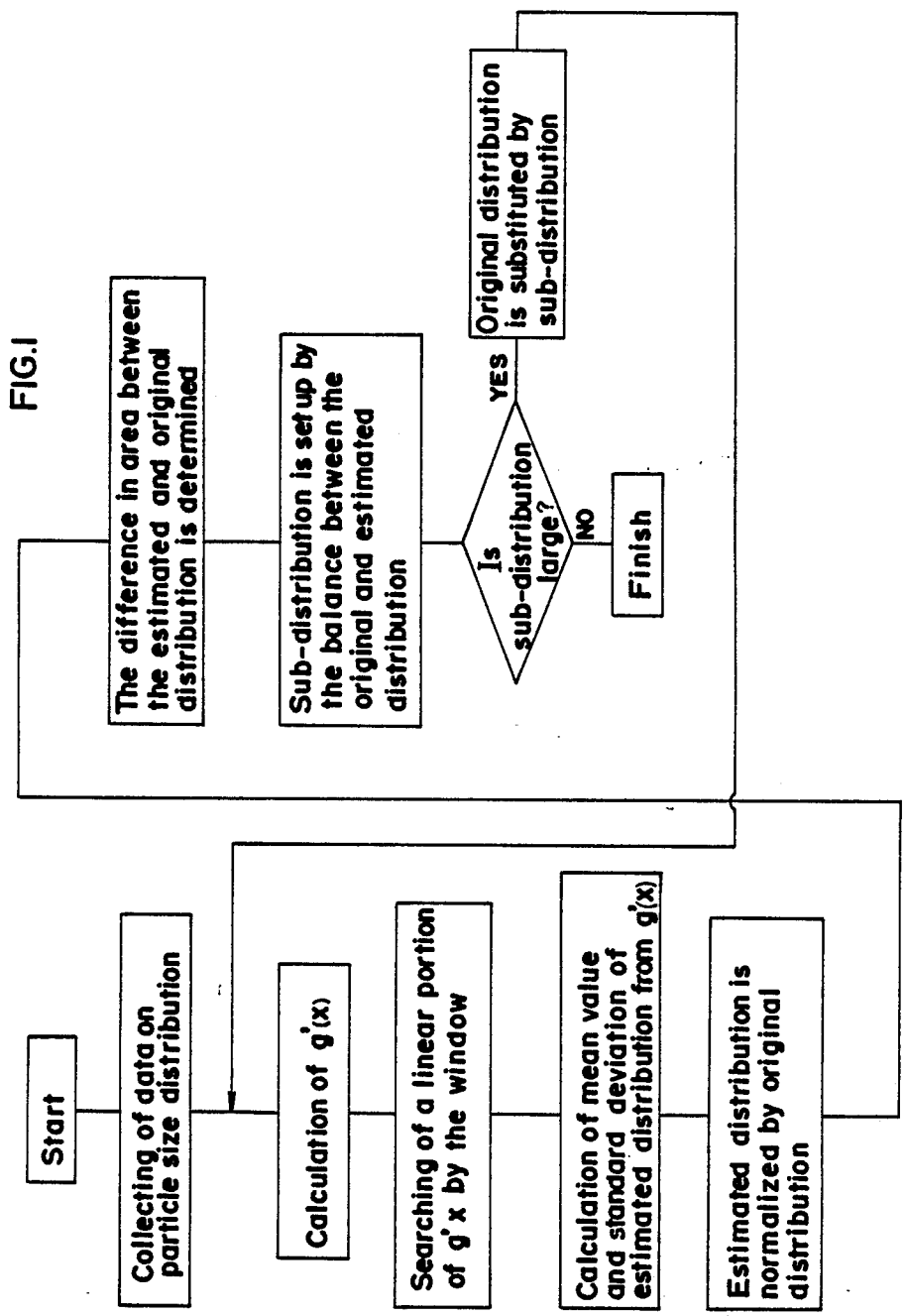
FIG. 1 is a flow chart showing a system embodying the present invention.

Referring to FIG. 1 the blood corpuscle pulses proportional to the volume are converted into a volume distribution by a comparator, the result of which is stored in a memory. The stored data is smoothed, which means that the noises contained in the particle size distribution are removed so as to facilitate the analysis of particle size. Then the natural logarithm is obtained for the particle size distribution, and the balance between the adjacent values on the X axis is calculated to determine the value of g'(x). In other words, as previously discussed, the natural logarithm g(x) is differentiated to obtain g'(x). Then a window (a range in which a treatment is applied to the X axis) is set so as to find a main portion of the given particle size distribution, and in this window a point (section) where the g'(x) (difference between adjacent values) becomes linear or approximately linear is determined. The value of the linear portion of g'(x) is expressed by a regression line equation, and from the inclination and segment of the equation, the mean value of the estimated particle size distribution and the standard deviation are calculated. These values obtained are introduced in the log-normal distribution, and the maximum value thereof is normalized by the original particle size distribution; that is, the maximum values of the original particle size distribution and estimated distribution are equalized, thereby facilitating the comparison therebetween. Thus, the actual measured data is used to determine the estimated particle size distribution. Then the difference in area between the two distributions is calculated to determine the matching distance (D).

The original particle size distribution is balanced by the estimated distribution to form a sub-distribution (the area of the original particle size distribution outside of the estimated distribution). If this sub-distribution has a sufficiently large area to allow another estimated distribution to be determined, the sub-distribution can be employed as the fresh original particle size distribution. This procedure is repeated.

When the area of the sub-distribution is small the operation is finished.

In one experiment, 2185 specimens of red blood cells were tested to find the matching distance (D), and it was found that they were distributed in a rather wide range of 0 to 400, showing a log-normal distribution.

Among the 2185 specimens, 6.9% thereof had a matching distance (D) of 100 or more, 82.1% of which were diagnosed as a malignant new organism and ulceration. The test revealed that 6.3% of the whole specimens suffered from these ailments. This proves that the method of the present invention can be used as a parameter for diagnosing patients' ailments through the diagnosis of blood.

Figure 2:
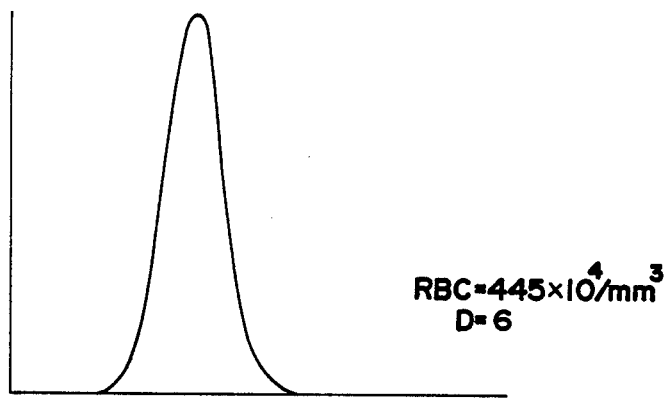
FIG. 2 is a graph showing an example analyzing normal red blood cells.

Referring to FIG. 2 the graph shows a case wherein:
Red Blood Cell (RBC)=445×10⁴/mm³
Matching distance (D)=6

In this graph the particle size distributions obtained and estimated distributions almost overlap, thereby resulting in a single curve.

Figure 3:
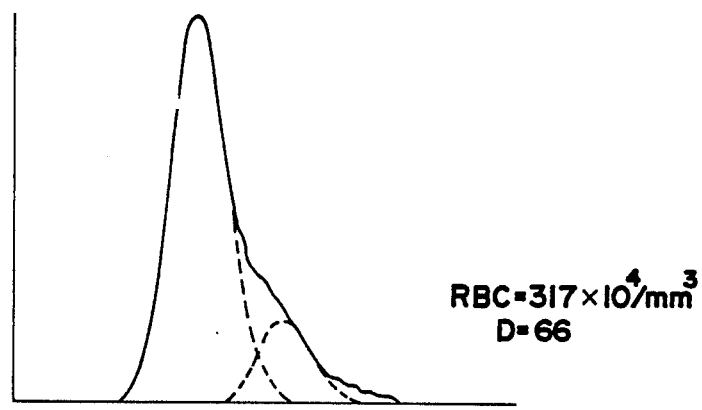
FIG. 3 is a graph showing an example analyzing red blood cells whose particle size distributions overlap each other.

Referring to FIG. 3 the graph shows an example of analysis of red blood cells whose particle size distributions overlap, wherein:
Red Blood Cells (RBC)=317×10⁴/mm³
Matching Distance (D)=66.

The dotted lines show the estimated particle size distribution.

Figure 4:
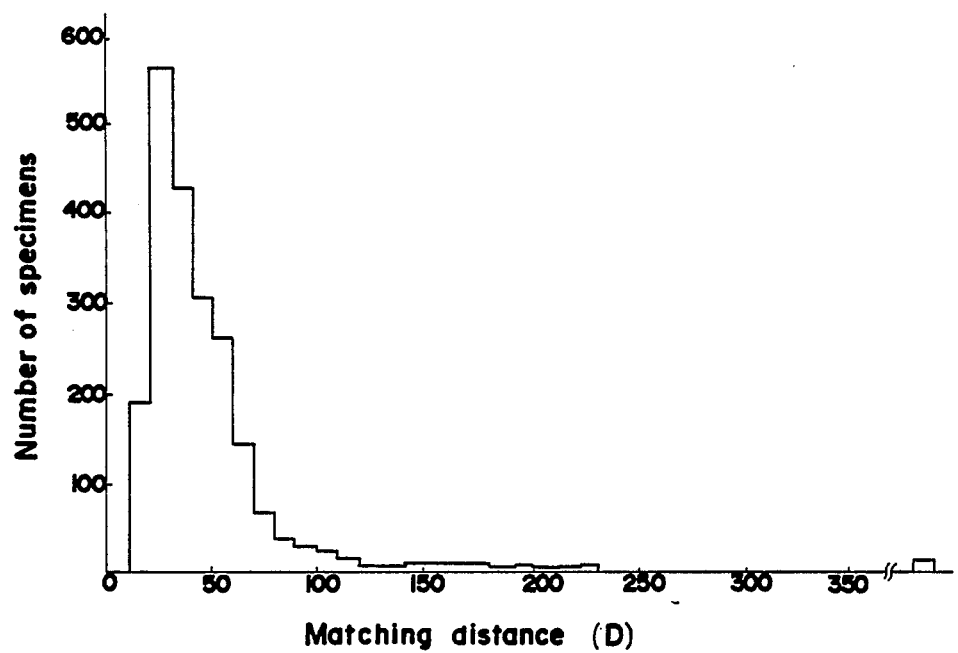
FIG. 4 is a graph showing the distribution of matching distance (D) obtained when the estimated particle size distribution is a log-normal distribution.

Referring to FIG. 4 the graph shows a relationship between the matching distance (D) and the number of specimens with respect to red blood cells, wherein the particle size distribution is a log-normal distribution. The same applies when the estimated particle size distribution is other than a log-normal distribution. The difference between the original particle size distribution and the estimated one can be represented by several parameters obtained from the following equation, wherein P is a matching ratio:

$$P = \int \left(\frac{f(x)}{h(x)}\right) dx$$

EXAMPLE 2

In Example (2) the method of the present invention was applied to the analysis of particle size distributions of red blood cells, employing a normal distribution and a alog-normal distribution. The normal distribution is given by the following equation:

$$f(x) = \frac{1}{\sigma\sqrt{2\pi}} \exp\left(-\frac{(X-\mu)^2}{2\sigma^2}\right)$$

wherein $\mu$ is a mean value, and $\sigma$ a standard deviation.

$$\ln f(x) = \ln \frac{1}{\sigma 2\pi} - \frac{(X-\mu)^2}{2\sigma^2}$$

$$= \ln \frac{1}{\sigma\sqrt{2\pi}} - \frac{X^2}{2\sigma^2} + \frac{\mu X}{\sigma^2} - \frac{\mu^2}{2\sigma^2}$$

g(x) is substituted by $\ln$ f(x).
Then, the above equation will be changed as follows:

$$g(x) = -\frac{1}{2\sigma^2} X^2 + \frac{\mu}{\sigma^2} X + \ln\frac{1}{\sigma\sqrt{2\pi}} - \frac{\mu^2}{2\sigma^2}$$

g(x) is differentiated:

$$g'(x) = -\frac{1}{\sigma^2} X + \frac{\mu}{\sigma^2}$$

$$= -\frac{1}{\sigma^2}(X-\mu)$$

Thus g'(x) is expressed by a linear expression which intersects the X axis at $\mu$, and which is inclined thereto at $-(1/\sigma^2)$. From this, the mean value $\mu$ and standard deviation $\sigma$ are calculated. In this way the normal log-distribution curve is estimated:

As an example of a parameter representing the difference between the estimated normal distribution and the original particle size distribution of blood corpuscles a matching distance (D) is introduced in the last-mentioned equation, wherein the matching distance (D) is expressed by:

$$D = \int (|f(x) - h(x)|) dX$$

wherein f(x) is a given distribution and h(x) is an estimated distribution.

Figure 5:
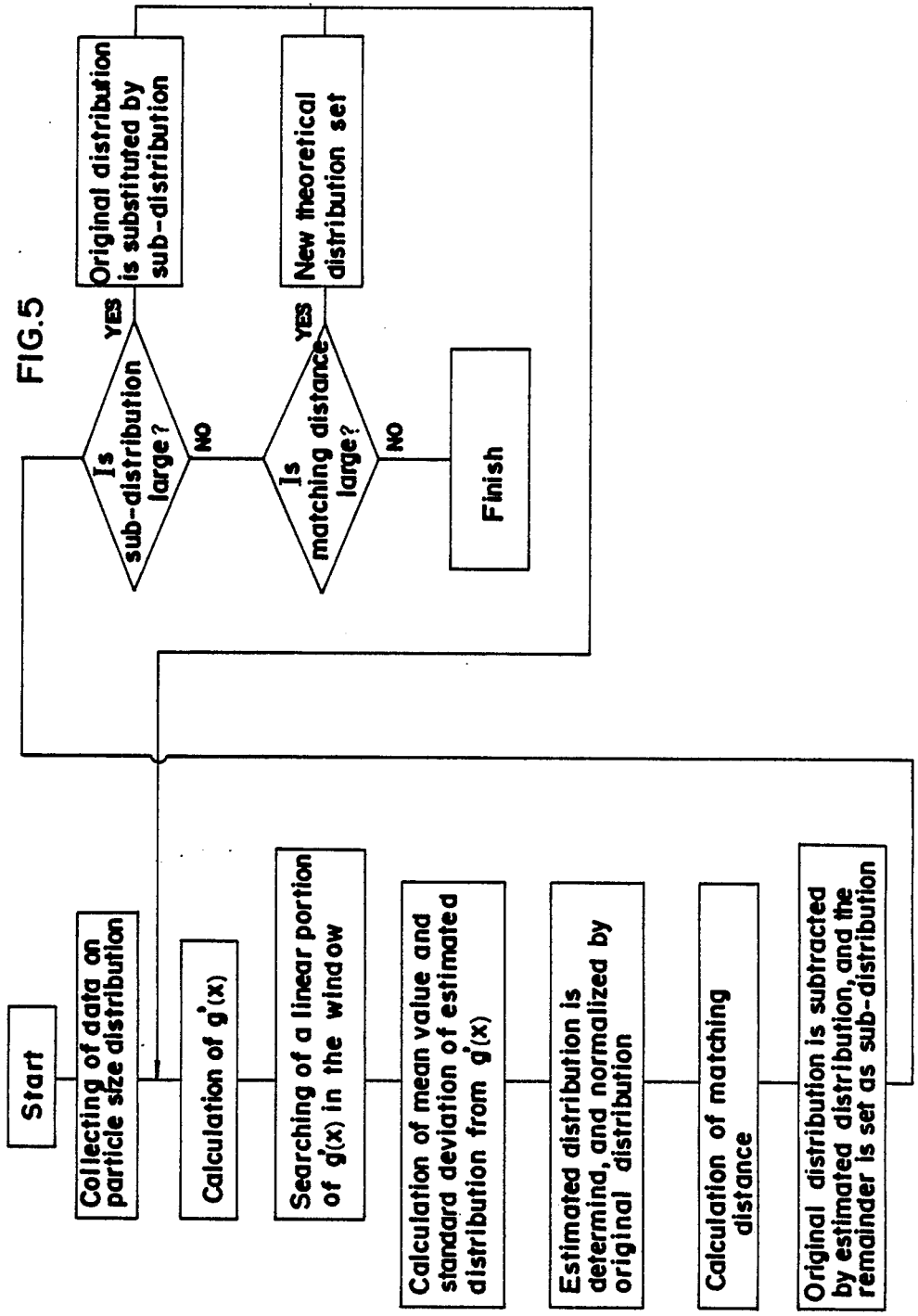
FIG. 5 is a flow chart showing a modified version of the system embodying the present invention.

Referring to FIG. 5, blood corpuscles pulses proportional to the volumes are converted into volume distributions by using a comparator, and stored in a memory. Then the data stored therein is smoothed as as to facilitate the analysis of particle size distribution. The smoothing is intended to remove noise components from the particle size distribution. Then the natural logarithm of each distribution is obtained and the difference between the adjacent values is calculated. As discussed above, this calculation is performed by differentiating the natural logarithm g(x). In this way g'(x) is calculated. A suitable window is set to find a main portion of the given distribution, and in this window a point (section) where g'(x) becomes linear or almost linear is determined. This point is the part of the particle size distribution which is identical with the normal distribution. A regression line equation of this linear portion of g'(x) is formulated, and from the inclination and segment of the curve the mean value and standard deviation of the estimated distribution are calculated. Then the mean value and standard deviation are introduced in the normal distribution, and the maximum value obtained is normalized by the original particle size distribution; that is, the maximum values of the original particle size distribution and estimated distribution are equalized, thereby facilitating the comparison therebetween. Then the difference in area between the two distributions is calculated to obtain a matching distance (D).

Figure 6:
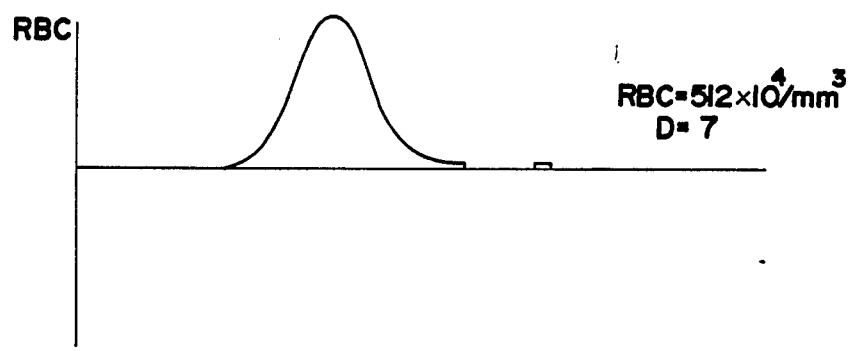
FIGS. 6 to 9 are graphs showing different examples of the analyses.
Figure 7:
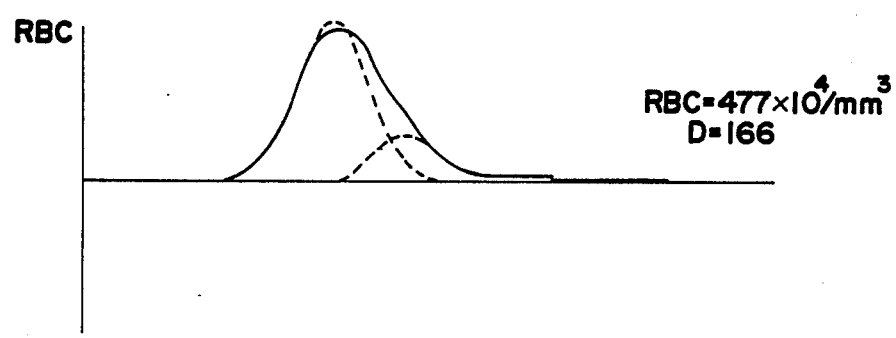
Figure 8:
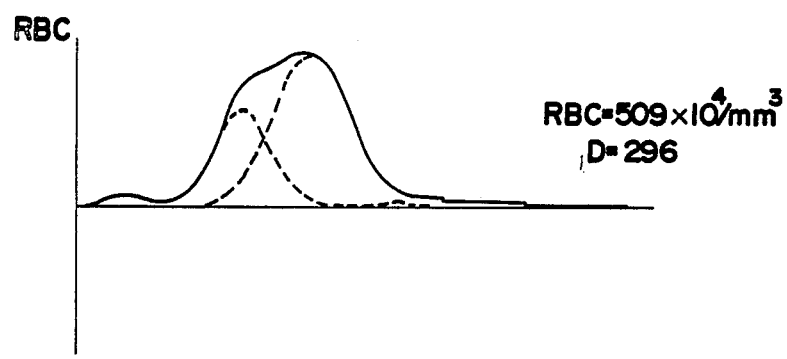

FIGS. 6, 7 and 8 show various types of graphs obtained when normal distributions are theoretically applied to analyze red blood cells; hereinafter these types will be referred to as Type I, Type II and Type III, respectively.

The graph shown in FIG. 6 almost overlaps the normal distribution. The dotted lines show the estimated particle size distribution which overlaps the original distribution to an undiscernible extent.

The graph shown in FIG. 7 shows a relatively large matching distance (D) and also shows that the distribution (indicated by the dotted lines) estimated from the normal distribution does not overlap the original distribution.

Figure 9:
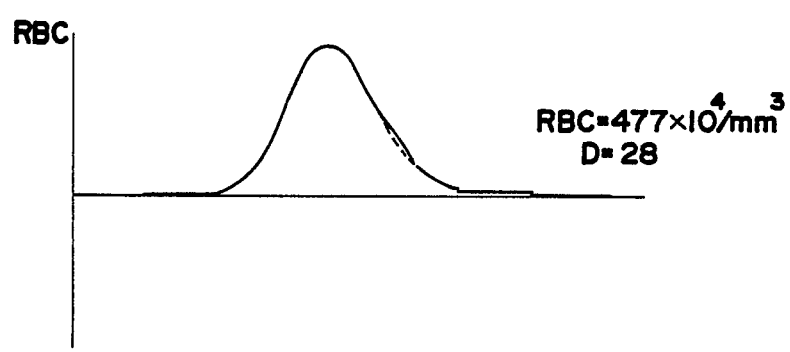

The graph shown in FIG. 9 has been obtained to estimate a particle size distribution by the use of a log-normal distribution as a theoretical distribution. This graph shows that the estimated distribution (indicated by the dotted lines) and the original distribution almost exactly overlap each other. It will be appreciated that the matching distance (D) is about 1/6 as short as in the case of the normal distribution.

FIG. 8 shows an example where there is a large space remaining after the estimation was made by a single normal distribution, thereby allowing a further estimation by the use of normal distribution. In other words, two normal distributions are allowed to estimate the distributions. This type of distribution is normally formed by the addition of the two normal distributions.

2500 specimens of blood were classified according to this type. As a result 51.3% belonged to Type I, 45.2% to Type II and 3.5% to Type III. Most of the blood belonging to Type III were found in the patients who suffered from the iron deficiency anemia.

325 specimens of blood were examined as to whether they had matching distance (D) of 60 or more under the normal distribution estimation and less than 60 under log-normal distribution estimation; as a result 39 specimens were selected, 35 specimens of which were collected from patients suffering from malignant new organism.

In this way the particle size distribution is classified by a theoretical distribution or else by a matching distance (D), which means that they can be useful as new parameters for diagnosing blood.

As mentioned above for parameters representing the difference between the estimated particle size distribution and the original one, the matching ratio (P) is expressed by the following equation:

$$P = \int \left( \frac{f(x)}{h(x)} \right) dx$$

As seen from the equation, various parameters can be used.

EXAMPLE 3

There is a log-normal distribution which satisfies the following equation:

$$f(x) = \frac{1}{x\sigma\sqrt{2\pi}} \exp\left( -\frac{(\ln x - \mu)^2}{2\sigma^2} \right)$$

wherein $\mu$ is a mean value, and $\sigma$ is a standard deviation.

Thus, the natural logarithm of f(x) is expressed by:

$$\begin{aligned} \ln f(x) &= \ln \frac{1}{x\sigma\sqrt{2\pi}} - \frac{(\ln x - \mu)^2}{2\sigma^2} \\ &= -\ln x + \ln \frac{1}{\sigma\sqrt{2\pi}} - \frac{(\ln x)^2}{2\sigma^2} + \frac{(\ln x)\mu}{\sigma^2} - \frac{\mu^2}{2\sigma^2} \end{aligned}$$

In the following discussion, X and g(x) are substituted by $\ln X$ and $\ln f(x)$, respectively.

Then $$g(x) = -\frac{1}{2\sigma^2} X^2 + \frac{\mu - \sigma^2}{\sigma^2} X + \ln \frac{1}{\sigma\sqrt{2\pi}} - \frac{\mu^2}{2\sigma^2}$$

As evident from this g(x) is expressed by a quadratic expression with respect to X. Then g(x) is differentiated as follows:

$$\begin{aligned} g'(x) &= -\frac{1}{\sigma^2} X + \frac{\mu - \sigma^2}{\sigma^2} \\ &= -\frac{1}{\sigma^2} (X - \mu + \sigma^2) \end{aligned}$$

Thus, g'(x) is expressed by a linear expression which intersects the X-axis at $\mu - \sigma^2$ and is inclined thereto at $-(1/\sigma^2)$. With the value of g'(x), the mean value $\mu$ and the standard deviation $\sigma$ are calculated, thereby estimating a log-normal distribution.

Figure 10:
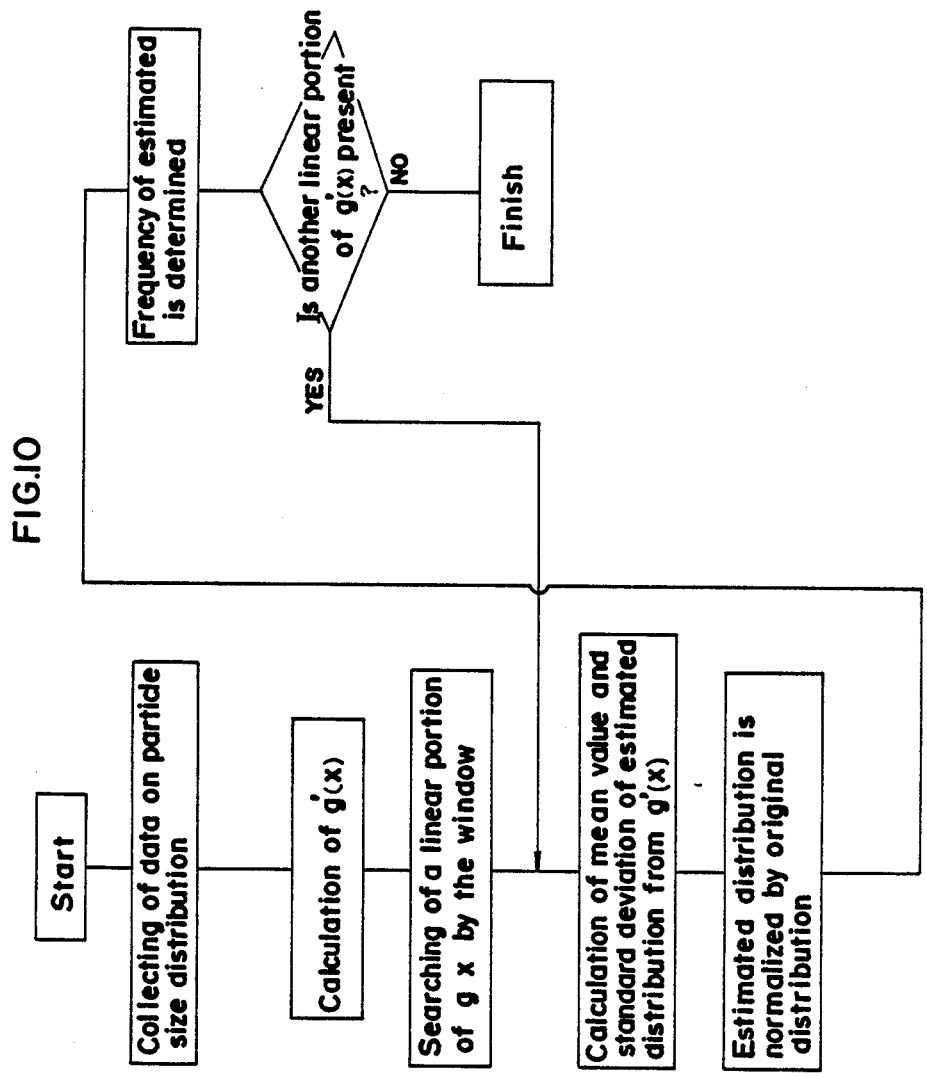
FIG. 10 is a flow chart showing a further modified version of the system embodying the present invention.
Figure 11:
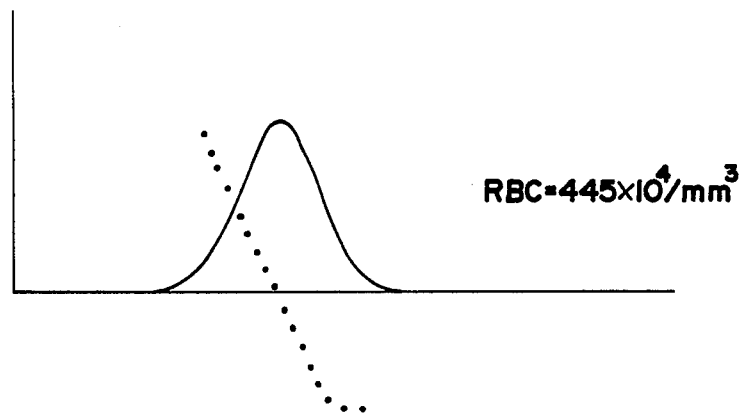
FIG. 11 is a graph made by plotting the values of g'(x)

Referring to FIG. 10, blood corpuscle pulses proportional to the volumes are converted into volume distribution by a comparator, and stored in a memory. The particle size distribution data stored therein are smoothed so as to facilitate the analysis of particle size distribution, which means that the noise components in the distribution are removed. Then the natural logarithm of the frequencies of particle size distribution, and the difference between the adjacent distributions is calculated. The calculated differences are divided by a balance between the logarithms of the corresponding ranks. The quotients are plotted against the logarithm of each rank, which is shown in FIG. 11. In this way g'(x) is calculated.

Figure 12:
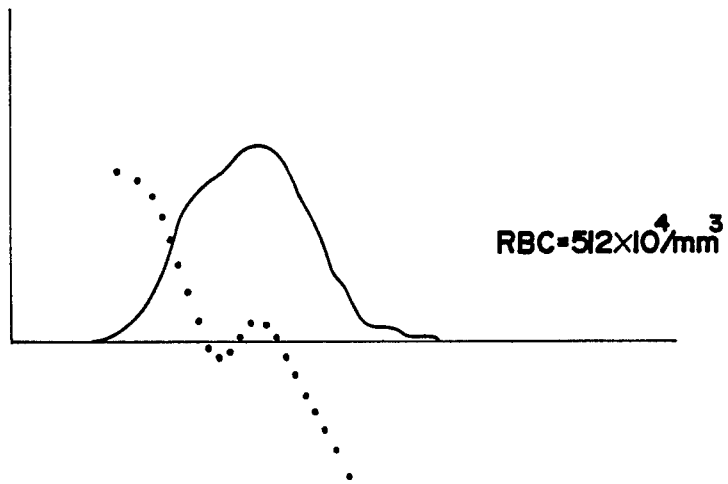
FIG. 12 is a graph showing an example in which the g'(x) has a plurality of linear portions.

FIG. 12 shows an example in which g'(x) has several linear portions. In this case there are two theoretical distributions available. To determine the linear portions of g'(x), a window is provided and shifted along the X-axis. In this way linear or approximately linear portions are extrapolated, and from the intersections of the X- and Y-axis the mean value and standard deviation are calculated. Then these values are introduced in the log-normal distribution and the maximum value is normalized by the original particle size distribution; that is, the maximum value is equalized to that of the original particle size distribution, thereby facilitating the comparison between the original particle size distribution and the estimated one. Then the frequency of the estimated particle size distribution is determined. The plurality of linear portions of g'(x) leads to a plurality of theoretical distrubutions. Therefore, on the basis of each linear portion an estimated distribution and the frequency are obtained. The obtained data is output to a CRT, printer or host computer.

Figure 13:
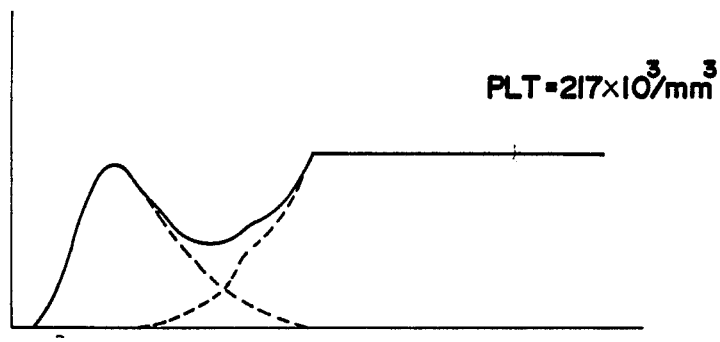
FIG. 13 is a graph showing an example in which a blood platelet portion overlaps the red blood cell portion.

The following cases are where the method is applied to blood corpuscles:

(1) A case where red blood cells overlap blood plate portions;

The graph of FIG. 13 shows an example where a red blood cell portion overlaps a blood platelet portion (PLT). The left-hand section shows the PLT portion, and the theoretical distribution is indicated by dotted lines. The right-hand section is the red blood cell portion, whose graph looks like a straight line because of the curve being cut away at a certain value. In view of the overlapping of the red blood cell portion and PLT portion the measured values obtained from the theoretical distribution was 163,000 PLTs, whereas that obtained by an ordinary threshold was 217,000 PTLs.

Figure 14:
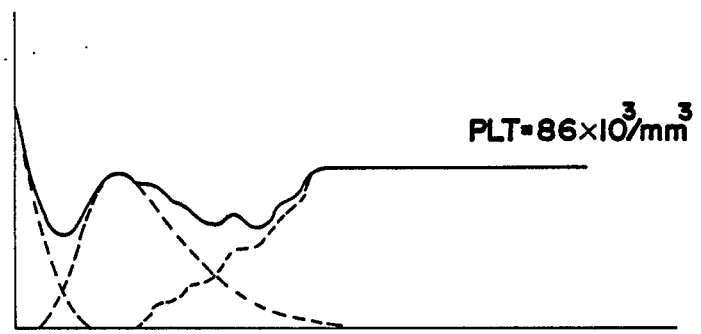
FIG. 14 is a graph showing an example in which there is little blood platelet portion.

(2) A case where a small quantiy of PLT is present:

When the blood has a small number of PLTs, such as some thousand to some ten-thousand PLTs, the impure factors such as noise adversely act, and lead to the inaccurate measurement, for which FIG. 14 shows an example. The left-hand section is a noise portion; the middle section is the PLT portion, and the right-hand section is a red blood cell portion. The theoretical distribution is shown by the dotted lines. The measured value from the theoretical distribution was 44,000 whereas that from an ordinary threshold was 86,000.

Figure 15:
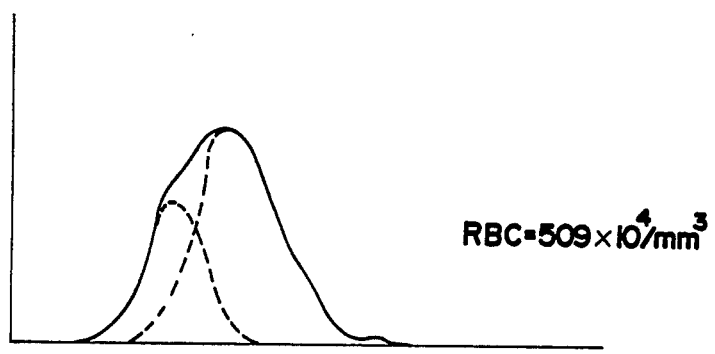
FIG. 15 is a graph showing an example of red blood cells having several theoretical distributions.

(3) A case where a red blood cell portion has two or more theoretical distributions:

Referring to FIG. 15 the theoretical distributions are shown by the dotted lines. The blood in this example contained different sizes of blood corpuscles because of transfusion, having 5,090,000 red blood cells (RBC), wherein the larger section had 3,660,000 RBCs and the smaller section had 1,420,000 RBCs.

As is evident from the foregoing description the method of the present invention has made it possible to remove irrelevant particles from the specimen particles, thereby securing a reliable measurement. When several distributions overlap, the present invention is particularly advantageous in measuring the respective distributions.

As referred to above the theoretical distribution can be a normal distribution or another. The method of the present invention can be equally applied to the analysis of latex particles, many kinds of cells or any other extremely fine particles.

The main advantages of the present invention are as follows:

(1) The adoption of a new parameter facilitates the recognition of characteristics of particle size distributions, and the collection of clinical data.

(2) An abnormality can be numerically represented, thereby securing the objectiveness of the data.

(3) The analysis of particle size distribution can be effectively conducted when several distributions overlap each other.

(4) The number of blood corpuscles can be counted accurately.

(5) The method of the present invention can be applied not only to blood corpuscles, but also to latex particles, cells or any other extremely fine particles.

(6) The counting of the particles can be conducted in a state free from noise or any other impure factors, thereby enhancing the accuracy and reliability of the data.

(7) The method of the invention can be carried out on a relatively small-size apparatus, such as a blood corpuscle counter, thereby making the method applicable at a limited space in hospitals and laboratories.

(8) In carrying out the method of the invention the particle size distribution to be diagnosed and the theoretical distribution to be used are simultaneously indicated, whereby the operator has an accurate information about them beforehand.

What is claimed is:

1. A method for measuring and analyzing particle size distribution, the method comprising:
    collecting an analyzing particle size distribution of a given sample content from a particle size measuring instrument;
    setting up an estimated particle size distribution as a theoretical distribution based upon portions of distributions for the given sample content particle size distribution;
    comparing between the analyzing particle size distribution and the estimated particle size distribution so as to determine the difference therebetween; and
    making the difference a characteristic parameter for classifying the analyzing particle size distribution according to the sample content.

2. A method as in claim 1, wherein the estimated distribution is output to an output section of an analyzing instrument simultaneously with the analyzing particle size distribution.

3. A method for measuring and analyzing particle size distribution, the method comprising:
    collecting an analyzing particle size distribution of a given sample content from a particle size measuring instrument;
    setting up an estimated particle size distribution as a theoretical distribution based upon portions of distributions for the given sample content particle size distribution;
    comparing between the analyzing particle size distribution and the estimated particle size distribution so as to set up a classifying characteristic parameter representing the difference therebetween; and
    classifying the analyzing particle size distribution according to the sample content depending upon at least one of the characteristic parameter and the type of estimated distribution.

4. A method as in claim 3, wherein the analyzing particle size distribution is compared to a plurality of estimated distributions.

5. A method as in claim 4, further including setting up said plurality of estimated particle size distributions as multiple theoretical distributions, comparing between said analyzing distributions and each of said plurality of estimated distributions to determine the difference between each of said plurality of estimated distributions and said analyzing distribution and making each difference a characteristic parameter for classifying the analyzing particle size distribution according to the sample content.

6. A method as in claim 5, wherein said setting up of said plurality of estimated particle size distributions includes setting up a given number of estimated particle size distributions as a function of said analyzing particle size distribution.

7. A method as in claim 6, wherein the estimated particle size distribution is used to obtain a characteristic parameter for classifying the collected analyzing particle size distribution.

8. A method for measuring and analyzing particle size distribution, the method comprising:
    collecting an analyzing particle size distribution of a given sample content from a particle size measuring instrument;
    setting up an estimated particle size distribution as a theoretical distribution;
    comparing between the analyzing particle size distribution and the estimated particle size distribution so as to determine the difference therebetween;
    making the difference a characteristic parameter for classifying the analyzing particle size distribution according to the sample content; and
    further including setting up a plurality of estimated particle size distributions as multiple theoretical distributions, comparing between said analyzing distribution and each of said plurality of estimated distributions to determine the difference between each of said plurality of estimated distributions and said analyzing distribution and making each difference a characteristic parameter for classifying the analyzing particle size distribution according to the sample content.

9. A method as in claim 8, wherein said setting up of said plurality of estimated particle size distributions includes setting up a given number of estimated particle size distributions as a function of said analyzing particle size distribution.

10. A method for measuring and analyzing particle size distribution the method comprising:
    collecting an analyzing particle size distribution from a particle size measuring instrument;
    setting up an estimated particle size distribution as a theoretical distribution as a function of said collected analyzing particle size distribution;
    wherein said analyzing particle size distribution includes a frequency component and a size component, said setting up of said estimated particle size distribution including:
    setting up a logarithm of said frequency of said analyzing particle size distribution;
    differentiating said logarithm of said frequency of said analyzing particle size distribution;
    finding a linear portion of said differentiated logarithm of said frequency of said analyzing particle size distribution;
    calculating a mean value and standard deviation from said linear portion; and
    determining said estimated particle size distribution using said calculated mean value and said standard deviation.

11. A method as in claim 10, wherein said differentiating of said logarithm of said frequency of said analyzing particle size distribution includes determining the difference between adjacent logarithm analyzing frequency distribution values.

12. A method as in claim 10, wherein said finding of said linear portion includes applying a window to said differentiated logarithm of said frequency of said analyzing particle size distribution.

13. A method as in claim 10, further including comparing between the analyzing distribution and the estimated distribution so as to determine the difference therebetween, and making the difference a characteristic parameter for classifying the analyzing particle size distribution according to the same content.

14. A method as in claim 13, further including setting up a plurality of estimated particle size distributions as multiple theoretical distributions, comparing between said analyzing distribution and each of said plurality of estimated distributions to determine the difference between each of said plurality of estimated distributions and said analyzing distribution and making each difference a characteristic parameter for classifying the analyzing particle size distribution according to the sample content.

15. A method as in claim 14, wherein said setting up of said plurality of estimated particle size distributions includes setting up a given number of estimated particle size distributions as a function of said analyzing particle size distribution.

16. A method as in claim 15, wherein said setting up of said plurality of estimated particle size distributions includes setting up a number of estimated particle size distributions corresponding to the number of linear portions of said differentiated logarithm of said frequency of said analyzing particle size distribution.

* * * * *